United States Patent [19]

Conti

[11] 4,148,907
[45] Apr. 10, 1979

[54] STEREOISOMERS OF 1-(1'BENZYL-2'PYRRYL)-2-DI-SEC.-BUTYLAMINOETHANOL AND PHARMACEUTICAL COMPOSITIONS COMPRISING SAME

[75] Inventor: Franco Conti, Milan, Italy
[73] Assignee: Etablissement Viridis, Liechtenstein
[21] Appl. No.: 852,685
[22] Filed: Nov. 18, 1977

[30] Foreign Application Priority Data

Nov. 18, 1976 [BE] Belgium ............................... 255466

[51] Int. Cl.² ..................... A61K 31/40; C07D 207/44
[52] U.S. Cl. ............................... 424/274; 260/326.5 L
[58] Field of Search .................. 260/326.5 L; 424/274

[56] References Cited

U.S. PATENT DOCUMENTS

| | | | |
|---|---|---|---|
| 3,558,652 | 1/1971 | Teotino et al. | 260/326.5 L |
| 3,629,435 | 12/1971 | Teotino et al. | 424/274 |
| 3,857,857 | 12/1974 | Bella et al. | 260/326.5 L |

FOREIGN PATENT DOCUMENTS

1154744  6/1969  United Kingdom.

Primary Examiner—Jose Tovar
Attorney, Agent, or Firm—Joseph W. Molasky

[57] ABSTRACT

Novel stereoisomers of 1-(1'-benzyl-2'pyrryl)-2-di-sec.-butylaminoethanol of the formula:

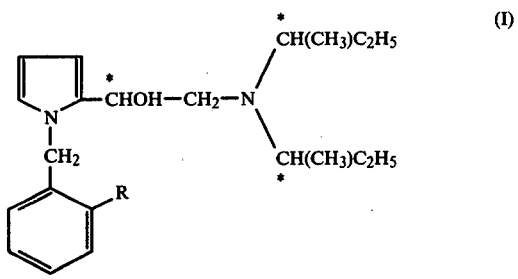

wherein R is fluoro or trifluoromethyl and the nontoxic therapeutically acceptable salts thereof; including pharmaceutical compositions comprising same. The said products and compositions have utility as analgesics.

4 Claims, No Drawings

STEREOISOMERS OF 1-(1'BENZYL-2'PYRRYL)-2-DI-SEC.-BUTYLAMINOETHANOL AND PHARMACEUTICAL COMPOSITIONS COMPRISING SAME

This invention relates to novel stereoisomers of a 1-(1'-benzyl-2'-pyrryl)-2-di-sec.-butylaminoethanol of the formula:

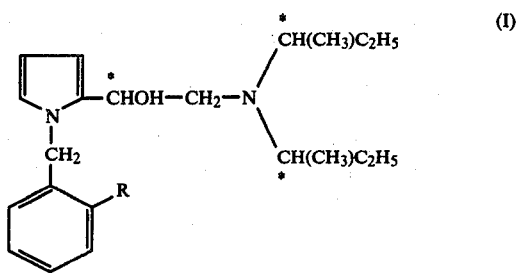

wherein R is fluoro or trifluoromethyl; to the non-toxic salts thereof and to pharmaceutical compositions comprising same as the active ingredient. The said products and compositions exhibit analgesic activity.

BACKGROUND

It is known from U.S. Pat. No. 3,629,435 that the following compounds possess analgesic activity:

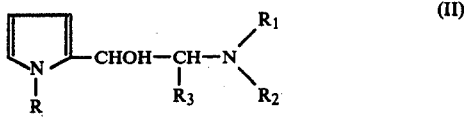

wherein R is benzyl or substituted benzyl. In this patent R is broadly defined but it appears that only a few substituted benzyl derivatives were actually prepared, specifically, only the ortho-chlorobenzyl derivatives among which 1-[1'(o-chlorobenzyl)-2'-pyrryl]-2-di-sec.-butylaminoethanol is named:

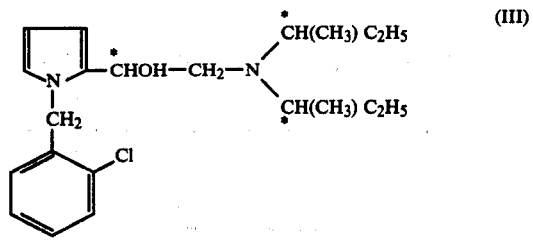

This compound is said to be the most active compound within the disclosed class of aminoethanols and it has been marketed as a valuable analgesic under the name "VIMINOLO" (W.H.O. Chronicle, 1970, N.3, list 25).

According to U.S. Pat. No. 3,629,435, the compounds II and III are prepared as a mixture of stereoisomers by reducing the corresponding keto precursors. Despite many attempts to resolve the said stereoisomeric mixture, which can be more or less complex because of the number of assymetric centers present in the molecule, it has been impossible up to now to do so.

The U.S. Pat. No. 3,857,857 describes a method for directly synthetizing each optical isomer of 1-[1'(o-chlorobenzyl)-2'-pyrryl]-2-di-sec.-butylaminoethanol (III) and using this method four isomers of optical purity were prepared and their analgesic activity determined.

From this determination it was found that one of the four isomers, identified in said Patent as Compound "R$_2$", is much more active than the other isomers and also, more active than the corresponding racemic compound "VIMINOLO".

THE INVENTION

It is an object of this invention to prepare two stereoisomers of optical purity never before prepared, not even as a racemic mixture.

These stereoisomers have the formula:

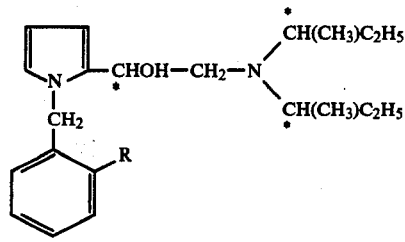

wherein R is fluoro or trifluoromethyl. These new compounds have quite surprisingly shown an analgesic effect of a much higher order than that exhibited by VIMINOLO and, also, higher than that of the "R$_2$" Compound commonly considered as the best of the class.

Moreover, this increase in activity is not accompanied, as is usually the case, by higher toxicity but, on the contrary, the new compounds have a reduced toxicity when compared against VIMINOLO and the "R$_2$" Compound.

The new compounds of this invention possess therapeutic indexes which are exceptional in the field of analgesic products.

These new compounds are prepared through a method of direct synthesis analogous to that described in U.S. Pat. No. 3,857,857 for the o-chloro-benzyl derivative.

This method comprises the following essential steps:

(1) Preparation of R,R(−) di-sec.-butylamine:

(a) R(−) sec.-butylamine is separated from the racemic sec.-butylamine by means of L(+) tartaric acid, according to the procedure described in Thome-Ber. 1903, 36, 582.

(b) The (−) sec.-butylamine thus obtained is treated with a racemic sec.-butyl derivative of the formula X-CH(CH$_3$)C$_2$H$_5$ wherein X is preferably bromo or chloro, in the presence of a polar organic solvent.

(c) The separation of the resulting R,R(−) di-sec.-butylamine hydrobromide or hydrochloride is performed by fractional crystallization from acetone or ethanol.

(2) Preparation of the chloroglyoxyl-pyrryl derivative:

A benzyl-pyrrole of the formula:

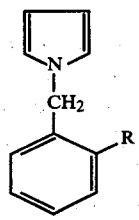

wherein R is fluoro or trifluoromethyl, is treated with oxalylchloride in the presence of an inert, anhydrous, organic solvent, at a temperature of −15° C., under stirring. There is thus obtained a compound of the formula:

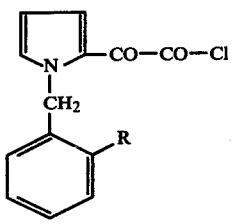

wherein R has the above-indicated meaning.

(3) Preparation of the pyrryl-glyoxylamide:

The chloroglyoxyl-pyrryl derivative obtained in the preceding step is treated with R,R(−) di-sec.-butylamine or an acid addition salt thereof in an inert organic solvent, at a temperature below 0° C. and in the presence of a basic substance suitable for blocking the formation of hydrohalogenic acid to afford N,N-di-sec.-butyl-1-(o-R-benzyl)-2-pyrryl-glyoxylamide.

(4) Preparation of the amino-pyrryl-ethanol derivative:

The N,N-di-sec.-butyl-1-(o-R-benzyl)-2-pyrryl-gloxyl amide obtained according to step (3) above is reduced by means of a metallo- or organo-metallo hydride, in the presence of an inert organic solvent at a temperature of between about 20° C. and the reflux temperature. There is thus obtained 1-[1′-(o-R-benzyl)-2′-pyrryl]-2-di-sec.-butylamino-(1R+1S) ethanol.

The mixture of the two diastereoisomers thus obtained is treated with p-hydroxybenzoic acid to afford the corresponding p-hydroxybenzoates and these are separated by fractional crystallization from a polar organic solvent, preferably, acetone.

By repeating the crystallization from acetone, the two diastereoisomers are obtained at practically 100% optical purity. Although it is not possible to state which of the two isomers has the (R) configuration and which possesses the (S) configuration, nevertheless, the two isomers have been isolated and identified.

Only one of said isomers, identified hereinafter as the one which precipitates upon cooling the diastereoisomeric solution in boiling acetone, is critical to this invention.

The absolute space configuration of the asymmetric carbon atoms indicated with an asterisk in the formula (I), is defined according to JUPAC Tentative Rules for the Monenclature of Organic Chemistry 1970, 35, 2849-2869.

The absolute configuration of di-sec.-butylamine is based on the absolute configuration of sec.-butylamine (see A. Kjaer, S. E. Hausen, Acta Chemica Scandinavia 1957, II - 1898).

The isomers of 1-[1′-(o-R-benzyl)-2′-pyrryl]-2-di-sec.-butylamino (1R+1S) ethanol, which have shown a surprising analgesic activity and which are thus the object of the present invention, are identified hereinafter in unequivocal manner through their physical characteristics.

Isomer A:

1-[1′-(o-fluorobenzyl)-2′-pyrryl]-2-di-(R,R)-sec.-butylaminoethanol; m.p. of p-hydroxybenzoate: 144°-145° C.

$[\alpha]_D^{20}$ (in methanol c=1%): −31° C.±3° C.
$[\alpha]_D^{20}$ (in methanol c=2%): −29° C.±3° C.
$[\alpha]_{436}^{20}$ (in methanol C=1%): −59° C.±3° C.
$[\alpha]_{436}^{20}$ (in methanol c=2%): −58° C.±3° C.

Isomer B:

1-[1′-(o-trifluoromethylbenzyl-2′-pyrryl]-2-di-(R,R)-sec.-butylaminoethanol: m.p. of p-hydroxybenzoate: 148°-150° C.

$[\alpha]_D^{20}$ (in methanol c=1%): −27° C.±3° C.
$[\alpha]_D^{20}$ (in methanol c=2%): −26° C.±3° C.
$[\alpha]_{436}^{20}$ (in methanol c=1%): −50° C.±3° C.
$[\alpha]_{436}^{20}$ (in methanol c=2%): −48° C.±3° C. The analgesic activity ($ED_{50}$) of isomers A and B has been determined via the hot plate test on mice (N/.B Eddy et Coll. J. Pharmacol. 98, 121, 1950) and via the "tail flick" test on rats (D'Amour and Smith; J. Pharmacol. 1941, 72, 74). The resulting values are set forth in the following Table and compared with the values given under identical conditions for VIMINOLO and the "R₂" Compound referred to hereinabove (Pharmacological Research Communications 8, 111 (1976)).

The acute toxicity values ($LD_{50}$) have been determined by the method of Litchfield and Wilcoxson (J. Pharmacol. 1949, 96, 99) both for the new compounds of this invention and for VIMINOLO and the "R₂" Compound.

| Compound | $ED_{50}$ mg/kg hot plate s.c | $ED_{50}$ mg/kg Tail Flick s.c. | $LD_{50}$ mg/kg i.p. | T.I. |
|---|---|---|---|---|
| Isomer A | 0.65 | 0.44 | 384 | 872 |
| Isomer B | 0.60 | 0.38 | 358 | 942 |
| "R₂" Compound | 1.15 | 0.71 | 230 | 324 |
| VIMINOLO |  | 12.5 | 167 | 13.36 |

From the above data it is evident that the analgesic activity of the new compounds A and B R+nearly twice that of the Compound "R₂" which in turn was surprisingly more active than VIMINOLO.

It is also apparent that the $LD_{50}$ is much higher for new compounds A and B, that is, they are much less toxic than the Compound "R₂" and VIMINOLO. The superiority of new Compounds A and B is also evident from the therapeutic indexes which have been calculated as a ratio of $LD_{50}/ED_{50'}$ taking as the $ED_{50}$ value that which is obtained by the tail flick test.

The new compounds of this invention can be administered per os, and by injection. The present compounds are useful in treating a number of diseases which cannot be satisfactorily treated with analgesics administered per os and which are thus slowly assumed by the organism.

This invention will now be described by reference to specific examples. However, it is to be understood that these examples are illustrative only and not limitative. Therefore, any substitution of equivalent materials or modification in the reaction conditions is considered as being within the scope of this invention and not a departure therefrom.

EXAMPLE 1

1-[1'-(o-Fluorobenzyl)-2'-Pyrryl]-2-Di-(R,R)-Sec.-Butylamino (1R+1S) Ethanol, p-Hydroxybenzoate Step A: R,R(−) Di-Sec.-Butylamine Hydrobromide R(−) sec.-butylamine is dissolved in absolute ethanol and to this solution is added (R+S) 2-bromobutane in excess and the resulting mixture is then refluxed over about 60 hours.

Following reflux the solution is hot filtered and the filtrate is cooled and then kept at −15° C. over about 48 hours. The resulting R,R(−) di-sec.-butylamine hydrobromide is separated by filtration and then purified by successive crystallization from acetone.

Step B: 1-(o-Fluorobenzyl)-2-Pyrrylglyoxylic Acid Chloride

A solution of oxalylchloride in anhydrous pentane is put into a flask provided with a stirrer, thermometer, reflux cooler and tube for nitrogen bubbling. The solution is maintained under a nitrogen atomosphere at −15° C.

A solution of 1-(o-fluorobenzyl)pyrrole in anhydrous pentane is then dropped into the flask with stirring.

The ratio between the reactants is on the order of about 1.5 moles of oxalyl chloride per mole of 1-(o-fluorobenzyl)pyrrole.

The temperature of the mixture is maintained at −15° C. for a few minutes after the addition of the 1-(o-fluorobenzyl)pyrrole is completed. Then the temperature is slowly raised to 40° C. under a slight vacuum and under a nitrogen stream to completely remove excess oxalyl chloride and solvent.

There is thus obtained a precipitate of 1-(o-fluorobenzyl)-2-pyrrylglyoxylic acid chloride.

Step C: N,N-Di-Sec.-Butylamide of 1-(o-Fluorobenzyl)-2-Pyrrylglyoxylic Acid 1-(o-Fluorobenzyl)-2-pyrrylglyoxylic acid chloride (26.5 g.) is dissolved in chloroform (200 ml.) and the resulting solution, cooled at −15° C., is added dropwise to a solution of R,R(−) di-sec.-butylamine hydrobromide (21 g.) and triethylamine (21 g.) in chloroform (200 ml).

The mixture is heated slowly up to 50° C., stirring is maintained for one hour and the mixture is then cooled and washed successively with water, sodium carbonate and water.

The organic layer is removed, dried over sodium sulphate and then evaporated to dryness.

The residue consists of crude (−) N,N-di-sec.-butylamide of 1-(o-fluorobenzyl)-2-pyrrylglyoxylic acid.

Step D: 1-[1'-(o-Fluorobenzyl)-2'-Pyrryl]-2-Di-(R,R)-Sec.-Butylamino (1R=1S) Ethanol, p-Hydroxybenzoate The (−) N,N-di-sec.-butylamide of 1-(o-fluorobenzyl)-2-pyrrylglyoxylic acid obtained as an impure product in Step C, is dissolved in anhydrous toluene (300 ml). and the resulting solution is introduced dropwise, with stirring, into a solution of LiAlH$_4$ and tetrahydrofuran in toluene. The LiAlH$_4$ constitutes about a 30% molar excess over the amide reactant.

The reaction mixture is maintained at 25°–30° C. until the addition of the reactants is completed and the mixture is then refluxed for one hour.

The mixture is then cooled, excess hydride is decomposed with water and sodium hydroxide (V. M. Micovic and M. C. J. Mihailovic J. Org. Chem. 1953, 1190) and the solvent is eliminated by evaporation.

An oily residue is obtained (24.5 g.) and this is dissolved in methylethylketone (200 ml.) and then treated with a solution of p-hydroxybenoic acid (14 g.) in methylethylketone (50 ml.).

The mixture is allowed to rest overnight and the resulting precipitate is filtered with a water vacuum-pump.

There is thus obtained 29.5 grams of 1-[1'-(o-fluorobenzyl)-2'-pyrryl]-2-di-(R,R)-sec.-butylamino (1R+1S) ethanol, p-hydroxybenzoate (m.p.: 128°–142° C. with decomposition).

The mixture of diastereoisomers thus obtained is dissolved in a strong excess of boiling acetone under stirring.

Upon cooling the acetonic solution to room temperature a crystalline product precipitates rich in one of the two diastereoisomers, namely, the isomer identified as A in this specification.

Upon crystallizing the precipitate three times, and upon cooling the boiling acetone solution, the compound A is obtained in the form of a pure p-hydroxybenzoate having a m.p. of 144°–145° C.

The specific rotatory power of the compound A with different polarized lights and at various concentrations are set forth hereinabove.

The method described in Example 1 was repeated in an identical manner, except that 1-(o-trifluoromethylbenzyl)pyrrole was substituted for the 1-(o-fluorobenzyl)pyrrole of Step B.

Upon the conclusion of this method, after several crystallizations from acetone, a single optically pure isomer was obtained from the mixture of diastereoisimers. This product is 1-[1'-(o-trifluoromethylbenzyl)-2'pyrryl]-2-di-(R,R)-sec.-butylaminoethanol.

The pure compound in the form of its p-hydroxybenzoate has a melting point of 148°–150° C. This product has been identified unequivocally through its rotatory power with different polarized lights at various concentrations.

What is claimed is:

1. An optically active isomer of the formula:

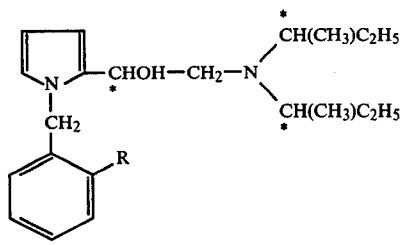

wherein R is fluoro or tifluoromethyl; and the non-toxic therapeutically acceptable acid addition salts thereof.

2. A 1-[1'-(o-Fluorobenzyl)-2'-pyrryl]-2-di-(R,R)-sec.-butylaminoethanol according to claim 1 of the formula:

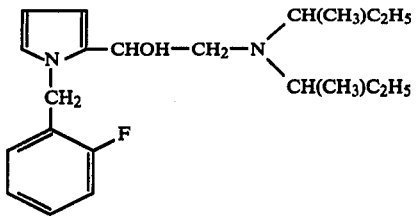

the p-hydroxybenzoate salt of which has a melting point of 144°–145° C. and the following values of specific rotatory power:

$[\alpha]_D^{20}$ (in methanol c=1%): $-31° \pm 3°$ C.

$[\alpha]_D^{20}$ (in methanol c=2%): $-29° \pm 30°$C.

$[\alpha]_{436}^{20}$ (in methanol c=1%): $-59° \pm 3°$ C.

$[\alpha]_{436}^{20}$ (in methanol c=2%): $-58° \pm 3°$ C.

3. A 1-[1'-(o-Trifluoromethylbenzyl)-2'-pyrryl]-2-di-(R,R)-sec.-butylaminoethanol according to claim 1 of the formula:

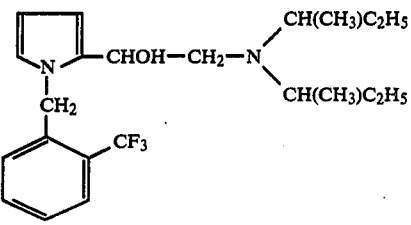

the p-hydroxybenzoate salt of which has a melting point of 148°–150° C. and the following values of specific rotatory power:

$[\alpha]_D^{20}$ (in methanol c=1%): $-27° \pm 3°$ C.

$[\alpha]_D^{20}$ (in methanol c=2%): $-26° \pm 3°$ C.

$[\alpha]_{436}^{20}$ (in methanol c=1%): $-50° \pm 3°$ C.

$[\alpha]_{436}^{20}$ (in methanol c=2%): $-48° \pm 3°$ C.

4. A therapeutic composition having analgesic activity which comprises as the active ingredient an essentially pure optically active isomer of the formula:

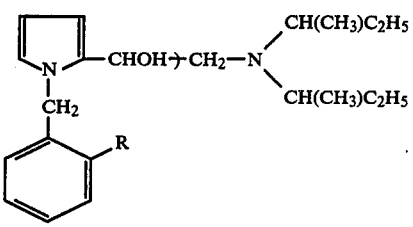

wherein R is fluoro or trifluoromethyl, or a non-toxic thereapeutically acceptable acid addition salt thereof; in combination with a pharmacologically acceptable carrier.

* * * * *